United States Patent
Retsina et al.

(10) Patent No.: US 9,347,176 B2
(45) Date of Patent: *May 24, 2016

(54) PROCESSES FOR PRODUCING CELLULOSE PULP, SUGARS, AND CO-PRODUCTS FROM LIGNOCELLULOSIC BIOMASS

(71) Applicant: API Intellectual Property Holdings, LLC, Atlanta, GA (US)

(72) Inventors: Theodora Retsina, Atlanta, GA (US); Vesa Pylkkanen, Atlanta, GA (US); Steven R. Rutherford, Peachtree City, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/044,784

(22) Filed: Oct. 2, 2013

(65) Prior Publication Data

US 2014/0096922 A1      Apr. 10, 2014

Related U.S. Application Data

(60) Provisional application No. 61/709,960, filed on Oct. 4, 2012, provisional application No. 61/781,635, filed on Mar. 14, 2013, provisional application No. 61/842,356, filed on Jul. 2, 2013.

(51) Int. Cl.
*D21B 1/02* (2006.01)
*D21C 1/02* (2006.01)
(Continued)

(52) U.S. Cl.
CPC ... *D21C 3/26* (2013.01); *C08B 1/00* (2013.01); *C08B 37/0057* (2013.01); *C08H 8/00* (2013.01); *D21B 1/02* (2013.01); *D21B 1/021* (2013.01);
(Continued)

(58) Field of Classification Search
CPC .......... D21B 1/02; D21B 1/021; D21C 11/00; D21C 11/0007
USPC ...................................... 162/24, 29
See application file for complete search history.

(56) References Cited

U.S. PATENT DOCUMENTS

| 5,424,417 | A | * | 6/1995 | Torget et al. | 536/56 |
| 5,865,949 | A | * | 2/1999 | Pere et al. | 162/24 |
| 7,943,008 | B2 | * | 5/2011 | Kirov et al. | 162/24 |

OTHER PUBLICATIONS

Smook, Handbook for Pulp and Paper Technologists, 1992, Angus Wilde Publications, 2nd edition, chapters 9 and 16.*

(Continued)

*Primary Examiner* — Anthony Calandra
(74) *Attorney, Agent, or Firm* — Ryan P. O'Connor

(57) ABSTRACT

The GreenBox+ technology is suitable to extract hemicellulose sugars prior to pulping of biomass into pulp products. The revenue obtainable from the sugar stream can significantly improve the economics of a pulp and paper mill. An initial extraction and recovery of sugars is followed by production of a pulp product with similar or better properties. Other co-products such as acetates and furfural are also possible. Some variations provide a process for co-producing pulp and hemicellulosic sugars from biomass, comprising: digesting the biomass in the presence of steam and/or hot water to extract hemicellulose into a liquid phase; washing the extracted solids, thereby generating a liquid wash filtrate and washed solids; separating the liquid wash filtrate from the washed solids; refining the washed solids at a refining pH of about 4 or higher, thereby generating pulp; and hydrolyzing the hemicellulose to generate hemicellulosic fermentable sugars.

18 Claims, 7 Drawing Sheets

(51) Int. Cl.
  *D21C 11/00* (2006.01)
  *D21C 3/26* (2006.01)
  *C08B 1/00* (2006.01)
  *C08B 37/00* (2006.01)
  *C08H 8/00* (2010.01)
  *D21C 3/02* (2006.01)
  *D21C 3/08* (2006.01)
  *D21C 3/20* (2006.01)
  *D21C 3/22* (2006.01)
  *C12P 19/14* (2006.01)

(52) U.S. Cl.
  CPC .. *D21C 1/02* (2013.01); *D21C 3/02* (2013.01); *D21C 3/08* (2013.01); *D21C 3/20* (2013.01); *D21C 3/222* (2013.01); *D21C 11/0007* (2013.01); *C12P 19/14* (2013.01)

(56) References Cited

OTHER PUBLICATIONS

Foekei et al., Improving Eucalyptus Pulp Refining Through the Control of Pulp Consistency and Stock pH: Comparisons at given bulk and given tensile strength, 1999, TAPPI Papermakers Conference proceedings.*

Foelkel at al., Improving Eucalyptus Pulp Refining Through the Control of Pulp Consistency and Stock pH. Comparisons at Given Bulk and Given Tensile Strength,1999, TAPPI Papermakers Conference.*

Smook, Handbook for Pulp and Paper Technologists, 1992, Angus Wilde Publications, 2nd edition, chapter 4.*

* cited by examiner

| COOKING TYPE | TIME (MIN) | TEMPERATURE (°C) | COOK YIELD, (%)[1] | SUGAR YIELD (% g SUGAR/g DRY WOOD)[1] | REFINING pH | PFI REVOLUTION | FREENESS (ml) | BREAKING LENGTH (km) | RING CRUSH (lbf/6 in) | CONCORA (lbf) |
|---|---|---|---|---|---|---|---|---|---|---|
| LHW | 5 | 190 | 76.3 / 80.6 | 12.4 / 11.1 | 4.17 | 5000 | 327 | 2.67 | 30 | 19 |
| LHW | 10 | 190 | 77.9 / 77.3 | 12.0 / 11.9 | 4.23 | 6000 | 313 | 2.45 | 30 | 23 |
| LHW | 15 | 190 | 81.0 / 76.7 | 10.7 / 11.6 | 4.20 | 6000 | 304 | 2.51 | 28 | 21 |
| LHW | 20 | 190 | 72.2 / 74.5 | 11.8 / 11.1 | 4.04 | 6000 | 321 | 2.24 | 27 | 22 |
| LHW | 25 | 190 | 73.1 / 72.5 | 9.2 / 9.5 | 3.94 | 6000 | 313 | 2.33 | 28 | 24 |
| LHW | 30 | 190 | 74.7 / 78.1 | 5.8 / 7.5 | 3.83 | 6000 | 307 | 2.28 | 28 | 24 |
| LHW | 35 | 190 | 73.7 / 81.2 | 5.8 / 4.9 | 3.85 | 5500 | 298 | 2.11 | 27 | 23 |
| LHW | 40 | 190 | 75.9 / 76.2 | 5.2 / 4.1 | 3.80 | 5000 | 301 | 2.24 | 28 | 26 |
| SODA | 50 | 180 | 85.3 / 86.9 | 2.9 / 2.7 | 6.00 | 5500 | 323 | 3.29 | 37 | 29 |

FIG. 5A

| COOKING TYPE | TIME (MIN) | TEMPERATURE (°C) | COOK YIELD (%)[1] | SUGAR YIELD (% g SUGAR/g DRY WOOD)[1] | REFINING pH | PFI REVOLUTION | FREENESS (ml) | BREAKING LENGTH (km) | RING CRUSH (lbf/6 in) | CONCORA (lbf) |
|---|---|---|---|---|---|---|---|---|---|---|
| LHW | 10 | 170 | 90.1 / 96.9 | 8.8 / 7.5 | 7.18 | 8500 | 316 | 3.65 | 39 | 32 |
| LHW | 2.5 | 180 | 92.6 / 93.0 | 3.1 / 4.4 | 7.05 | 23750 | 290 | 3.48 | 43 | 33 |
| LHW | 5 | 180 | 91.7 / 90.5 | 7.7 / 8.6 | 7.25 | 10000 | 297 | 4.35 | 46 | 37 |
| LHW | 2.5 | 190 | 89.8 / 90.1 | 8.7 / 9.5 | 7.05 | 7250 | 312 | 3.64 | 40 | 32 |
| LHW | 5 | 190 | 86.9 / 86.4 | 10.7 / 12.0 | 7.06 | 5500 | 292 | 3.42 | 35 | 29 |
| SODA | | | 88.1 / 89.1 | 1.4 / 1.2 | 7.13 | 5500 | 314 | 3.55 | 40 | 32 |

FIG. 5B

| NO. | CHIPS DRY WT (g) | TEMP (°C) | TIME (MIN) | WET COOKED CHIPS WT (g) | PAN WT (g) | PAN + WET CHIPS (g) | O.D. PAN + CHIPS (g) | CHIPS CONSISTENCY | COOK YIELD BASED ON CHIPS WT | COOK & WASH LIQUOR (ml) | TOTAL SUGAR AFTER HYDROLYSIS (g) | SUGAR YIELD (g SUGAR/g DRY WOOD) | SUGAR YIELD (% g SUGAR/g DRY WOOD) |
|---|---|---|---|---|---|---|---|---|---|---|---|---|---|
| 1 | 141.75 | 190 | 2.5 | 347.5 | 2.2747 | 15.1764 | 6.9995 | 36.6% | 89.8% | 780 | 12.4 | 0.087 | 8.7% |
| 2 | 96.39 | 190 | 2.5 | 225.2 | 2.2772 | 15.1773 | 7.2644 | 38.6% | 90.1% | 630 | 9.2 | 0.095 | 9.5% |
| 3 | 141.75 | 180 | 2.5 | 349.9 | 2.2642 | 15.2042 | 7.121 | 37.5% | 92.6% | 790 | 4.4 | 0.031 | 3.1% |
| 4 | 96.56 | 180 | 2.5 | 238.9 | 2.2504 | 14.818 | 6.9743 | 37.6% | 93.0% | 620 | 4.3 | 0.044 | 4.4% |
| 5 | 141.75 | 180 | 5 | 345.6 | 2.2676 | 16.636 | 7.6712 | 37.6% | 91.7% | 800 | 11.0 | 0.077 | 7.7% |
| 6 | 96.56 | 180 | 5 | 233.7 | 2.2557 | 15.2405 | 7.1084 | 37.4% | 90.5% | 630 | 8.3 | 0.086 | 8.6% |
| 7 | 141.75 | 170 | 5 | 346.4 | 2.2412 | 15.9282 | 7.7653 | 40.4% | 98.6% | 880 | 4.2 | 0.030 | 3.0% |
| 8 | 96.39 | 190 | 5 | 230.3 | 2.2586 | 14.8325 | 6.8333 | 36.4% | 86.9% | 610 | 10.3 | 0.107 | 10.7 |
| 9 | 96.39 | 190 | 5 | 236.4 | 2.2699 | 15.9348 | 7.0812 | 35.2% | 86.4% | 640 | 11.5 | 0.120 | 12.0% |
| 10 | 96.39 | 170 | 10 | 234 | 2.2577 | 15.9301 | 7.3296 | 37.1% | 90.1% | 600 | 8.5 | 0.088 | 8.8% |
| 11 | 96.39 | 170 | 10 | 228.2 | 2.2771 | 15.191 | 7.5652 | 40.9% | 96.9% | 670 | 7.2 | 0.075 | 7.5% |

FIG. 6

PROCESSES FOR PRODUCING CELLULOSE PULP, SUGARS, AND CO-PRODUCTS FROM LIGNOCELLULOSIC BIOMASS

PRIORITY DATA

This patent application is a non-provisional application claiming priority to U.S. Provisional Patent App. No. 61/709,960, filed Oct. 4, 2012; U.S. Provisional Patent App. No. 61/781,635, filed Mar. 14, 2013; and U.S. Provisional Patent App. No. 61/842,356, filed Jul. 2, 2013. Each of these provisional patent applications is hereby incorporated by reference herein.

FIELD

The present invention generally relates to improved processes for producing cellulose pulp while recovering fermentable sugars from lignocellulosic biomass.

BACKGROUND

In recent years, the GreenPower+ technology has been developed by American Process, Inc. (API). GREEN POWER+ is a registered trademark of API, Registration No. 4062241. GreenPower+ technology is a patented technology for the production of low-cost sugars from the hemicelluloses of any type of biomass, including hardwoods, softwoods, and agricultural residues. The GreenPower+ process produces low-cost $C_5$ and $C_6$ sugars from the hemicelluloses of biomass feedstocks. These sugars are co-produced along with biomass power, pellets, or pulp. Essentially, sugars are extracted from the solids which are then utilized for existing applications, in synergy with pulp mills, pellet mills, biomass-based renewable power plants, and many other existing sites. Value is added while minimizing capital costs for commercial implementation, which may be retrofits, capacity additions, or greenfield sites. When applied to a pulping operation, the GreenPower+ technology is also known as GreenBox+™ technology. GREENBOX+ is a trademark of API, Serial No. 86000173.

It would be desirable to retrofit existing pulp mills with a GreenBox+ process. The revenue obtainable from the sugar stream can significantly improve the economics of a pulp and paper mill. Ideally, an initial extraction and recovery of sugars is followed by a pulping process that produces a pulp product with equivalent or similar properties, or potentially even better properties for certain downstream products. Besides sugars, other co-products become possible, in particular acetates since hemicellulose has a high concentration of acetyl groups that are released as acetic acid during sugar extraction.

In addition to the potential for higher revenue, there is also potential for reduced costs. For example, if the GreenBox+ process can replace a chemical pulping method, the chemical recovery cycle may be eliminated. There may also be environmental compliance benefits and reduced costs for compliance.

To date, there has been limited commercial success in extracting hemicellulose prior to pulping. Further improvements are needed to establish an economic process.

SUMMARY

Some variations provide a process for co-producing pulp and hemicellulosic sugars from biomass, the process comprising:

(a) providing lignocellulosic biomass comprising cellulose, hemicellulose, and lignin;
(b) digesting the biomass in the presence of steam and/or hot water to extract at least a portion of the hemicellulose into a liquid phase, thereby generating extracted solids;
(c) optionally separating at least some of the liquid phase from the extracted solids;
(d) washing the extracted solids with water at a washing pH of about 7 or less, thereby generating a liquid wash filtrate and washed solids;
(e) separating at least some of the liquid wash filtrate from the washed solids;
(f) refining the washed solids at a refining pH of about 4 or higher, thereby generating pulp; and
(g) hydrolyzing the hemicellulose contained in the liquid phase and/or in the liquid wash filtrate, in the presence of a hydrolysis catalyst, to generate hemicellulosic sugars.

In some embodiments, step (b) is conducted at a digestor temperature selected from about 140° C. to about 220° C., such as from about 170° C. to about 190° C. In some embodiments, step (b) is conducted at a digestor residence time selected from about 1 minute to about 60 minutes, such as from about 2 minutes to about 10 minutes.

In some embodiments, step (b) is conducted at a digestor pH from about 2 to about 6, such as from about 3 to about 5. In various embodiments, the refining pH is selected from about 5 to about 9, such as about 6 to about 8, or about 6.5 to about 7.5. The refining pH will generally be higher than the digestor pH, following pH adjustment with a suitable base. It is possible, however, for the digestor pH to be higher than the refining pH, or for the digestor pH and refining pH to be similar.

In certain embodiments, step (b) comprises introducing a sulfur-containing compound selected from the group consisting of sulfur dioxide, sulfurous acid, sulfuric acid, lignosulfonic acid, and combinations or derivatives thereof.

The pulp yield on biomass may vary from about 75% to about 95% (or higher) by weight. In some embodiments, the pulp yield on biomass is at least 85% or at least 90% by weight. In certain embodiments that achieve only mild extraction of hemicelluloses, the pulp yield on biomass is higher than 95%, such as about 96%, 97%, 98%, or 99% by weight.

In some embodiments, the washing in step (d) utilizes fresh water. In these or other embodiments, the washing in step (d) may utilize recycled water, which is preferably alkali-free recycled water to reduce or avoid alkaline degradation of sugars.

In some embodiments, steps (b) and (d) are carried out in a single unit. For example, a continuous countercurrent unit may be configured for both digestion and washing of solids.

When step (c) is carried out, the liquid phase and the liquid wash filtrate may be separately processed. Alternatively, the liquid phase and the liquid wash filtrate may be combined for the hydrolyzing in step (g). When step (c) is not carried out, the liquid phase (from digestion) forms part of the liquid wash filtrate, which also includes wash water.

In some embodiments, the hydrolysis catalyst comprises one or more compounds selected from the group consisting of sulfur dioxide, sulfurous acid, sulfuric acid, lignosulfonic acid, and combinations or derivatives thereof. In other embodiments, the hydrolysis catalyst comprises hemicellulase enzymes.

Some variations of the invention provide a process for co-producing pulp and hemicellulosic sugars from biomass, the process comprising:

(a) providing lignocellulosic biomass comprising cellulose, hemicellulose, and lignin;

(b) digesting the biomass in the presence of steam and/or hot water to extract at least a portion of the hemicellulose into a liquid phase, thereby generating extracted solids;
(c) optionally separating at least some of the liquid phase from the extracted solids;
(d) washing the extracted solids with water at a washing pH selected from about 7 or less, thereby generating a liquid wash filtrate and washed solids;
(e) separating at least some of the liquid wash filtrate from the washed solids;
(f) further digesting the extracted solids and/or the washed solids using a chemical pulping method, thereby generating digested solids;
(g) refining the digested solids at a refining pH selected from about 4 or higher, thereby generating pulp; and
(h) hydrolyzing the hemicellulose contained in the liquid phase and/or in the liquid wash filtrate, in the presence of a hydrolysis catalyst, to generate hemicellulosic sugars.

In some embodiments, the chemical pulping method is selected from the group consisting of Kraft pulping, sulfite pulping, soda pulping, and organosolv pulping. In certain embodiments, soda pulping is employed to further digest the extracted solids, the washed solids, or both of these.

Some variations of the invention provide a process for co-producing pulp and hemicellulosic sugars from biomass, the process comprising:
(a) providing lignocellulosic biomass comprising cellulose, hemicellulose, and lignin;
(b) digesting the biomass in the presence of steam and/or hot water to extract at least a portion of the hemicellulose into a liquid phase, thereby generating extracted solids;
(c) optionally separating at least some of the liquid phase from the extracted solids;
(d) washing the extracted solids with water at a washing pH selected from about 7 or less, thereby generating a liquid wash filtrate and washed solids;
(e) separating at least some of the liquid wash filtrate from the washed solids;
(f) refining the washed solids at a refining pH selected from about 4 or higher, thereby generating pulp;
(g) further digesting the pulp using a chemical pulping method; and
(h) hydrolyzing the hemicellulose contained in the liquid phase and/or in the liquid wash filtrate, in the presence of a hydrolysis catalyst, to generate hemicellulosic sugars.

In some embodiments, the chemical pulping method is selected from the group consisting of Kraft pulping, sulfite pulping, soda pulping, and organosolv pulping. In certain embodiments, soda pulping is employed to further digest the pulp.

In some variations, a process for producing pulp from biomass comprises:
(a) providing lignocellulosic biomass comprising cellulose, hemicellulose, and lignin;
(b) digesting the biomass in the presence of steam and/or hot water to extract at least a portion of the hemicellulose into a liquid phase, thereby generating extracted solids;
(c) optionally separating at least some of the liquid phase from the extracted solids;
(d) washing the extracted solids with water at a washing pH of about 7 or less, thereby generating a liquid wash filtrate and washed solids;
(e) separating at least some of the liquid wash filtrate from the washed solids;
(f) refining the washed solids at a refining pH of about 4 or higher, thereby generating pulp; and
(g) recovering or further processing the pulp.

The pulp from any of the disclosed processes may be combined with a second source of cellulose fiber prior to downstream processing of the pulp. The second source of cellulose fiber may be selected from, but is not limited to, OCC pulp, Kraft pulp, sulfite pulp, soda pulp, NSSC pulp, and organosolv pulp.

The pulp from any of the disclosed processes may be characterized by a concora of about 25 lbf or higher, such as about 32 lbf or higher. The pulp from any of the disclosed processes may be characterized by a ring crush strength of about 25 (lbf/6 in) or higher, such as about 40 (lbf/6 in) or higher. The pulp from any of the disclosed processes may be characterized by a breaking length of about 2.0 km or higher, such as about 3.6 km or higher.

Optionally, at least a portion of the pulp may be hydrolyzed to generate glucose.

In some embodiments, the process further comprises recovering an acetate co-product (using e.g. reverse osmosis), such as potassium acetate or sodium acetate.

Some variations provide a process for producing hemicellulosic sugars from biomass, the process comprising:
(a) providing lignocellulosic biomass comprising cellulose, hemicellulose, and lignin;
(b) digesting the biomass in the presence of steam and/or hot water to extract at least a portion of the hemicellulose into a liquid phase, thereby generating extracted solids;
(c) optionally separating at least some of the liquid phase from the extracted solids;
(d) washing the extracted solids with water at a washing pH of about 7 or less, thereby generating a liquid wash filtrate and washed solids; and
(e) hydrolyzing the hemicellulose contained in the liquid phase and/or in the liquid wash filtrate, in the presence of a hydrolysis catalyst, to generate hemicellulosic sugars.

Preferably, the process (in any embodiment) includes process integration of mass and/or energy involving at least two steps of said process. In some embodiments, the process includes process integration of mass and/or energy involving at least three steps of said process. Several examples of process integration are disclosed in the detailed description below.

For example, process integration may include recycling evaporator condensates may be recycled for use in step (b); recycling evaporator condensates may be recycled for use in one or more washing steps; integration with downstream operations involving the pulp, during or after step (g); concentrating fermentable sugars, recovering a condensate stream therefrom, and introducing the condensate stream to another location with a water requirement; sterilizing a fermentor or fermentor feed stream with a vapor take-off from one or more evaporators; and/or concentrating a fermentation product in a non-externally-heated effect of a multiple-effect evaporation unit.

The invention provides pulp intermediates or products produced by processes as described. The invention also provides consumer products (e.g., paper or corrugated medium) produced from the pulp intermediate or product. Also provided are hemicellulosic sugar intermediates or products produced by the disclosed processes. Fermentation products may be produced from the hemicellulosic sugar intermediates or products.

BRIEF DESCRIPTION OF THE FIGURES

FIG. 5A summarizes pulp physical properties measured from laboratory-scale experiments for a range of hot-water-extraction pulping conditions.

FIG. 5B summarizes pulp physical properties measured from laboratory-scale experiments for a range of hot-water-extraction pulping conditions.

FIG. 6 summarizes data collected with respect to the hemicellulose stream extracted during experimental hot-water-extraction pulping.

DETAILED DESCRIPTION OF SOME EMBODIMENTS

Figure 1:
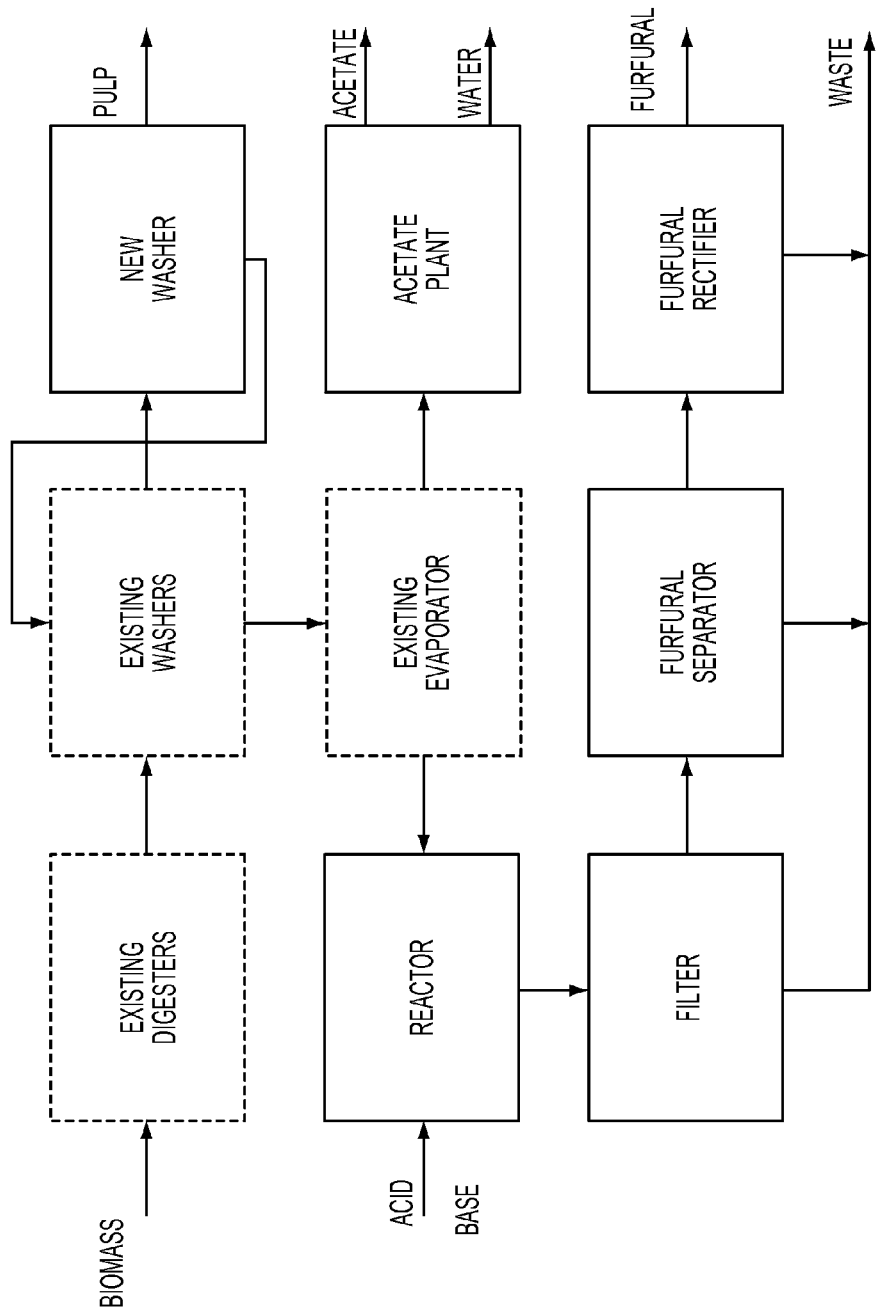
FIG. 1 is a high-level block-flow diagram according to some retrofit embodiments of the invention.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Some variations of the present invention are premised on the surprising discovery that steam or hot-water extraction of biomass is an effective pulping step to produce a pulp product, such as a chemical or semi-chemical pulp material, while also producing a hemicellulose sugar stream. Through experimentation, the inventors have determined suitable conditions for hot-water extraction as well as suitable downstream conditions and overall process configurations for co-producing pulp and sugars.

The biomass feedstock may be selected from hardwoods, softwoods, forest residues, industrial wastes, consumer wastes, or combinations thereof. Exemplary biomass feedstocks include maple, birch, and aspen. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof.

Some variations provide a process for co-producing pulp and hemicellulosic sugars from biomass, the process comprising:

(a) providing lignocellulosic biomass comprising cellulose, hemicellulose, and lignin;

(b) digesting the biomass in the presence of steam and/or hot water to extract at least a portion of the hemicellulose into a liquid phase, thereby generating extracted solids;

(c) optionally separating at least some of the liquid phase from the extracted solids;

(d) washing the extracted solids with water at a washing pH of about 7 or less, thereby generating a liquid wash filtrate and washed solids;

(e) separating at least some of the liquid wash filtrate from the washed solids;

(f) refining the washed solids at a refining pH of about 4 or higher, thereby generating pulp; and (g) hydrolyzing the hemicellulose contained in the liquid phase and/or in the liquid wash filtrate, in the presence of a hydrolysis catalyst, to generate hemicellulosic sugars.

In some embodiments, step (b) is conducted at a digestor temperature selected from about 140° C. to about 220° C., such as from about 170° C. to about 190° C. In some embodiments, step (b) is conducted at a digestor residence time selected from about 1 minute to about 60 minutes, such as from about 2 minutes to about 10 minutes.

In some embodiments, step (b) is conducted at a digestor pH from about 2 to about 6, such as from about 3 to about 5. In various embodiments, the refining pH is selected from about 5 to about 9, such as about 6 to about 8, or about 6.5 to about 7.5. The refining pH will generally be higher than the digestor pH, following pH adjustment with a suitable base. It is possible, however, for the digestor pH to be higher than the refining pH, or for the digestor pH and refining pH to be similar.

In certain embodiments, step (b) comprises introducing a sulfur-containing compound selected from the group consisting of sulfur dioxide, sulfurous acid, sulfuric acid, lignosulfonic acid, and combinations or derivatives thereof. In these embodiments, the digestor pH may be less than 2, such as about 1.5, 1, 0.5, 0 or less.

The pulp yield on biomass may vary from about 75% to about 95% (or higher) by weight. The yield is the fraction of starting solids remaining after pulping and washing, on a dry basis. In some embodiments, the pulp yield on biomass is at least 85% or at least 90% by weight. In certain embodiments that target mild extraction of hemicelluloses, the pulp yield on biomass is higher than 95%, such as about 96%, 97%, 98%, or 99% by weight. When the biomass yield is high, relatively little hemicelluloses are extracted. It can nevertheless be advantageous to extract a small quantity of hemicelluloses under mild conditions.

In some embodiments, the washing in step (d) utilizes fresh water. In these or other embodiments, the washing in step (d) may utilize recycled water, which is preferably alkali-free recycled water to reduce or avoid alkaline degradation of sugars. "Alkali-free recycled water" means that no alkali metal, or a base, salt, or derivative thereof (e.g., sodium hydroxide or potassium chloride) is introduced into the recycled water prior to use for washing. If desired, the pH of the wash water may be adjusted or maintained in the range of about 4 to 9, such as about 4.5, 5, 5.5, 6, 6.5, 6.6, 6.7, 6.8, 6.9, 7.0, 7.1, 7.2, 7.3, 7.4, 7.5, 8, or 8.5. For example, a fresh water source at a pH of about 8 may be adjusted with an acid to a pH of about 6 for washing. Or a recycled water stream at a pH of about 4 may be adjusted to a pH of about 7 for washing.

In some embodiments, steps (b) and (d) are carried out in a single unit. For example, a continuous countercurrent unit may be configured for both digestion and washing of solids. Multiple units may be employed in parallel, where each unit is configured for both digestion and washing. Or, a first unit may be configured for only digestion, with a downstream unit configured for both digestion and washing. Or, a first unit may be configured for both digestion and washing, followed by a downstream washing-only unit. Many variations are possible.

When step (c) is carried out, the liquid phase and the liquid wash filtrate may be separately processed. Alternatively, the liquid phase and the liquid wash filtrate may be combined for the hydrolyzing in step (g). When step (c) is not carried out, the liquid phase (from digestion) forms part of the liquid wash filtrate. That is, the digestor liquor is fed forward, without solid-liquid separation, to washing. Additional wash water is added, depending on the desired amount of washing and the washing efficiency of the washing unit. The digestor liquor therefore becomes combined (and diluted) with the added wash liquid.

Step (g) is desirable to increase the yield of fermentable sugars, by hydrolyzing (with water) the soluble oligomers into monomers. In some embodiments, the hydrolysis catalyst comprises one or more compounds selected from the group consisting of sulfur dioxide, sulfurous acid, sulfuric acid, lignosulfonic acid, and combinations or derivatives thereof. In other embodiments, the hydrolysis catalyst comprises hemicellulase enzymes or other enzymes capable of catalyzing hydrolysis of hemicellulose. In certain embodiments, step (g) is not performed and the hemicellulose oligomers (with some monomers typically present) recovered for sale or later processing.

Some variations of the invention provide a process for co-producing pulp and hemicellulosic sugars from biomass, the process comprising:
(a) providing lignocellulosic biomass comprising cellulose, hemicellulose, and lignin;
(b) digesting the biomass in the presence of steam and/or hot water to extract at least a portion of the hemicellulose into a liquid phase, thereby generating extracted solids;
(c) optionally separating at least some of the liquid phase from the extracted solids;
(d) washing the extracted solids with water at a washing pH selected from about 7 or less, thereby generating a liquid wash filtrate and washed solids;
(e) separating at least some of the liquid wash filtrate from the washed solids;
(f) further digesting the extracted solids and/or the washed solids using a chemical pulping method, thereby generating digested solids;
(g) refining the digested solids at a refining pH selected from about 4 or higher, thereby generating pulp; and
(h) hydrolyzing the hemicellulose contained in the liquid phase and/or in the liquid wash filtrate, in the presence of a hydrolysis catalyst, to generate hemicellulosic sugars.

Some variations of the invention provide a process for co-producing pulp and hemicellulosic sugars from biomass, the process comprising:
(a) providing lignocellulosic biomass comprising cellulose, hemicellulose, and lignin;
(b) digesting the biomass in the presence of steam and/or hot water to extract at least a portion of the hemicellulose into a liquid phase, thereby generating extracted solids;
(c) optionally separating at least some of the liquid phase from the extracted solids;
(d) washing the extracted solids with water at a washing pH selected from about 7 or less, thereby generating a liquid wash filtrate and washed solids;
(e) separating at least some of the liquid wash filtrate from the washed solids;
(f) refining the washed solids at a refining pH selected from about 4 or higher, thereby generating pulp;
(g) further digesting the pulp using a chemical pulping method; and
(h) hydrolyzing the hemicellulose contained in the liquid phase and/or in the liquid wash filtrate, in the presence of a hydrolysis catalyst, to generate hemicellulosic sugars.

In some embodiments, the chemical pulping method is selected from the group consisting of Kraft pulping, sulfite pulping, soda (sodium carbonate, $Na_2CO_3$) pulping, and organosolv pulping. In certain embodiments, soda pulping is employed to further digest the extracted solids, the washed solids, or both of these.

The pulp from any of the disclosed processes may be combined with a second source of cellulose fiber prior to downstream processing of the pulp. The second source of cellulose fiber may be selected from, but is not limited to, OCC pulp, Kraft pulp, sulfite pulp, soda pulp, NSSC pulp, or organosolv pulp.

The pulp from any of the disclosed processes may be characterized by a concora of about 25 lbf or higher, such as about 26, 27, 28, 29, 30, 31, 32, 33, 34, 35, 36, 37 lbf or higher. The pulp from any of the disclosed processes may be characterized by a ring crush strength of about 25 (lbf/6 in) or higher, such as about 40 (lbf/6 in) or higher. The pulp from any of the disclosed processes may be characterized by a breaking length of about 2.0 km or higher, such as about 2.1, 2.2, 2.3, 2.4, 2.5, 2.6, 2.7, 2.8, 2.9, 3.0, 3.1, 3.2, 3.3, 3.4, 3.5, 3.6 km or higher.

The invention provides pulp intermediates or products produced by processes as described. Using well-known techniques, consumer products (e.g., paper or corrugated medium) may be produced from the pulp intermediate or product. See, for example, Twede and Selke, "Cartons, crates and corrugated board: handbook of paper and wood packaging technology," DEStech Publications, pages 41-56, 2005; and Foster, "Boxes, Corrugated" in The Wiley Encyclopedia of Packaging Technology, 1997, eds. Brody A and Marsh K, 2nd ed.

Optionally, at least a portion of the pulp may be hydrolyzed to generate glucose. For example, pulp having inferior properties (such as fiber length or strength) may be hydrolyzed to glucose using cellulase enzymes or an acid catalyst (e.g., sulfuric acid). In some embodiments, the entire pulp product is hydrolyzed to glucose to maximize sugar production, either as a transient operation or as a steady-state operation.

The hemicellulosic sugars may be recovered in purified form, as a sugar slurry or dry sugar solids, for example. Any known technique may be employed to recover a slurry of sugars or to dry the solution to produce dry sugar solids. Thus the invention provides hemicellulosic sugar intermediates or products produced by the disclosed processes. In certain embodiments, the extracted hemicellulose stream is combusted for energy, or discarded.

Fermentation products may be produced from the hemicellulosic sugar intermediates or products. In some embodiments, the hemicellulose sugars are fermented to ethanol, 1-butanol, isobutanol, acetic acid, lactic acid, succinic acid, or any other fermentation product. A purified product may be produced by distillation, which will also generate a distillation bottoms stream containing residual solids. A bottoms evaporation stage may be used, to produce residual solids. Residual solids (such as distillation bottoms) may be recovered, or burned to produce energy for the process.

In some embodiments, the process further comprises recovering an acetate co-product, such as potassium acetate or sodium acetate. The process may include evaporation of hydrolysate to remove some or most of the volatile acids. The evaporation step is preferably performed below the acetic acid dissociation pH of 4.8, such as about 1.0, 1.5, 2.0, 2.5, 3.0, 3.5, 4.0, or 4.5. In certain embodiments, the process further comprises combining, at a pH of about 4.8 to 10 or higher, a portion of the vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered by reverse osmosis or other membrane separation or filtration (see, for example, U.S. Pat. No. 8,211,680 which is incorporated by reference). If desired, purified acetic acid may be generated from the alkaline acetate. Acetic acid and acetate salts have a number of known commercial uses.

Some embodiments also recover a furfural co-product. When furfural is desired, the conditions of the initial extraction and/or the hemicellulose hydrolysis may be more severe (compared to sugars production) so that $C_5$ sugars are converted to furfural. Under conditions of heat and acid, xylose and other five-carbon sugars undergo dehydration, losing three water molecules to become furfural ($C_5H_4O_2$). Hydrogenation of furfural provides furfuryl alcohol, which is a useful chemical intermediate and which may be further hydrogenated to tetrahydrofurfuryl alcohol. Furfural is used to make other furan chemicals, such as furoic acid, via oxidation, and furan via decarbonylation.

In some embodiments, additional evaporation steps may be employed. These additional evaporation steps may be conducted at different conditions (e.g., temperature, pressure, and pH) relative to the first evaporation step.

Some embodiments employ reaction conditions and operation sequences described in U.S. Pat. No. 8,211,680, issued Jul. 3, 2012; and/or U.S. patent application Ser. Nos. 13/471,662; 13/026,273; 13/026,280; 13/500,917; 61/536,477; 61/612,451; 61/612,453; 61/624,880; 61/638,730; 61/641,435; 61/679,793; 61/696,360; 61/709,960. Each of these commonly owned patents and patent applications is hereby incorporated by reference herein in its entirety. In some embodiments, the process is a variation of the GreenPower+ or GreenBox+ process technology which is commonly owned with the assignee of this patent application.

Effective "hot-water extraction" (or "HWE") conditions may include contacting the lignocellulosic biomass with steam (at various pressures in saturated, superheated, or supersaturated form) and/or hot water. In some embodiments, the HWE step is carried out using liquid hot water at a temperature from about 140-220° C., such as about 150° C., 160° C., 170° C., 175° C., 180° C., 185° C., 190° C., 200° C., or 210° C. In some embodiments, the HWE step is carried out using liquid hot water with a residence time from about 1 minute to about 60 minutes, such as about 2, 2.5, 3, 3.5, 4, 5, 7.5, 10, 12.5, 15, 20, 25, 30, 35, 40, 45, 50, or 55 minutes.

FIG. 1 is a high-level block-flow diagram according to some embodiments. Wood is fed to one or more digestors, which may be existing digestors in a retrofit of an existing pulp mill, for example. Existing washer(s) and evaporator(s) may also be utilized. In the embodiments depicted in FIG. 1, pulp is the primary product and acetate and furfural are co-products.

Figure 2:
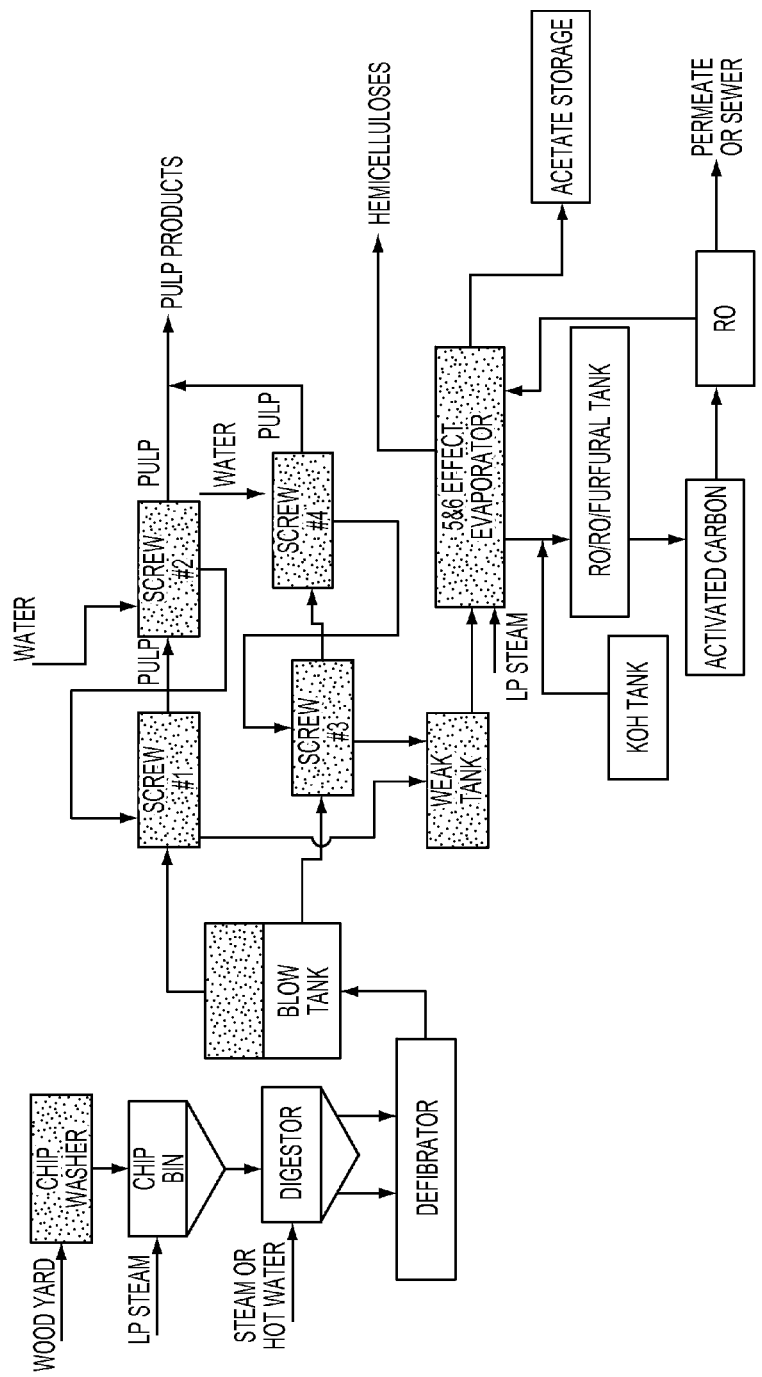
FIG. 2 is a simplified process-flow diagram for the production of pulp, hemicelluloses, and acetates, in some embodiments.
Figure 3:
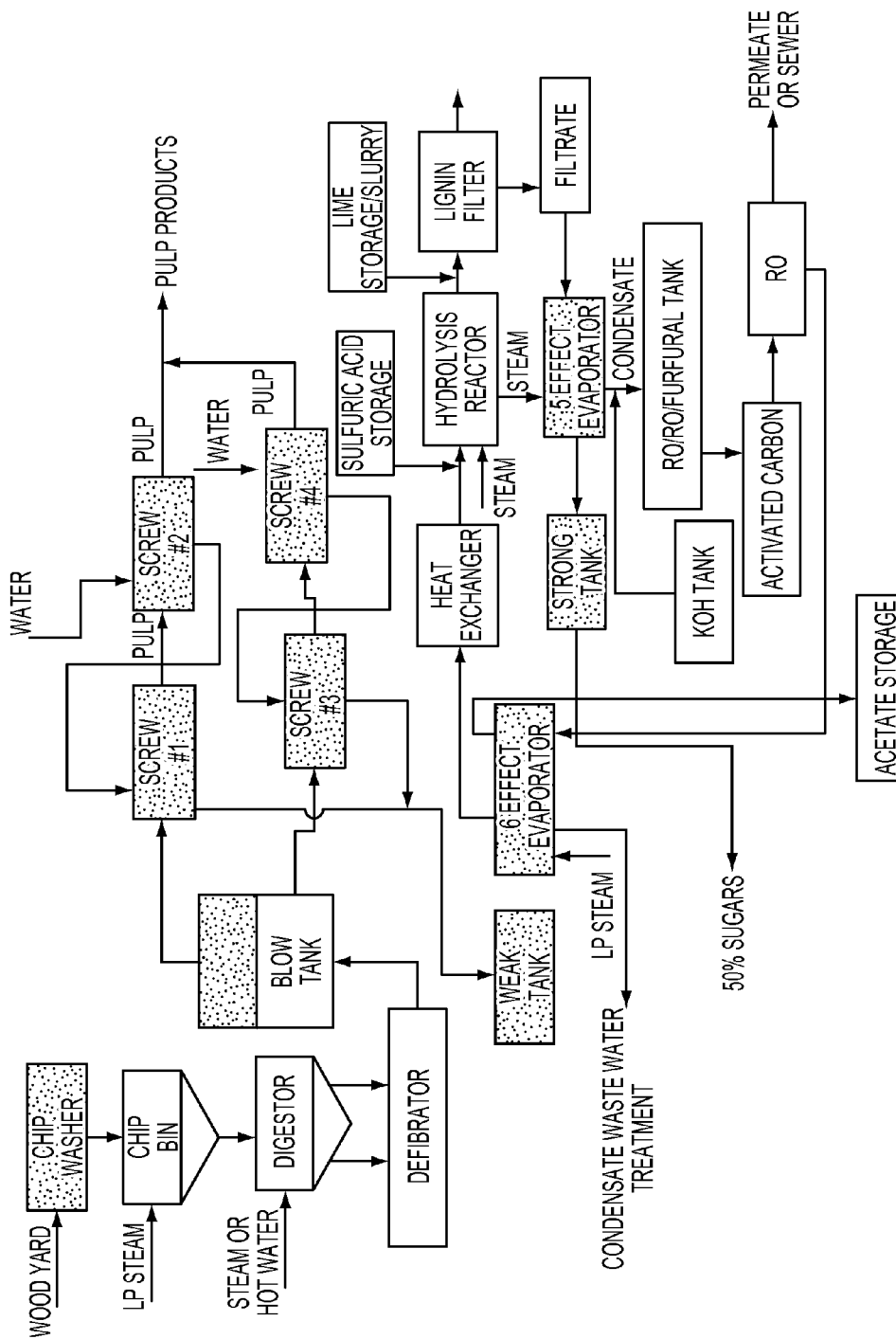
FIG. 3 is a simplified process-flow diagram for the production of pulp, sugars, and acetates, in some embodiments.
Figure 4:
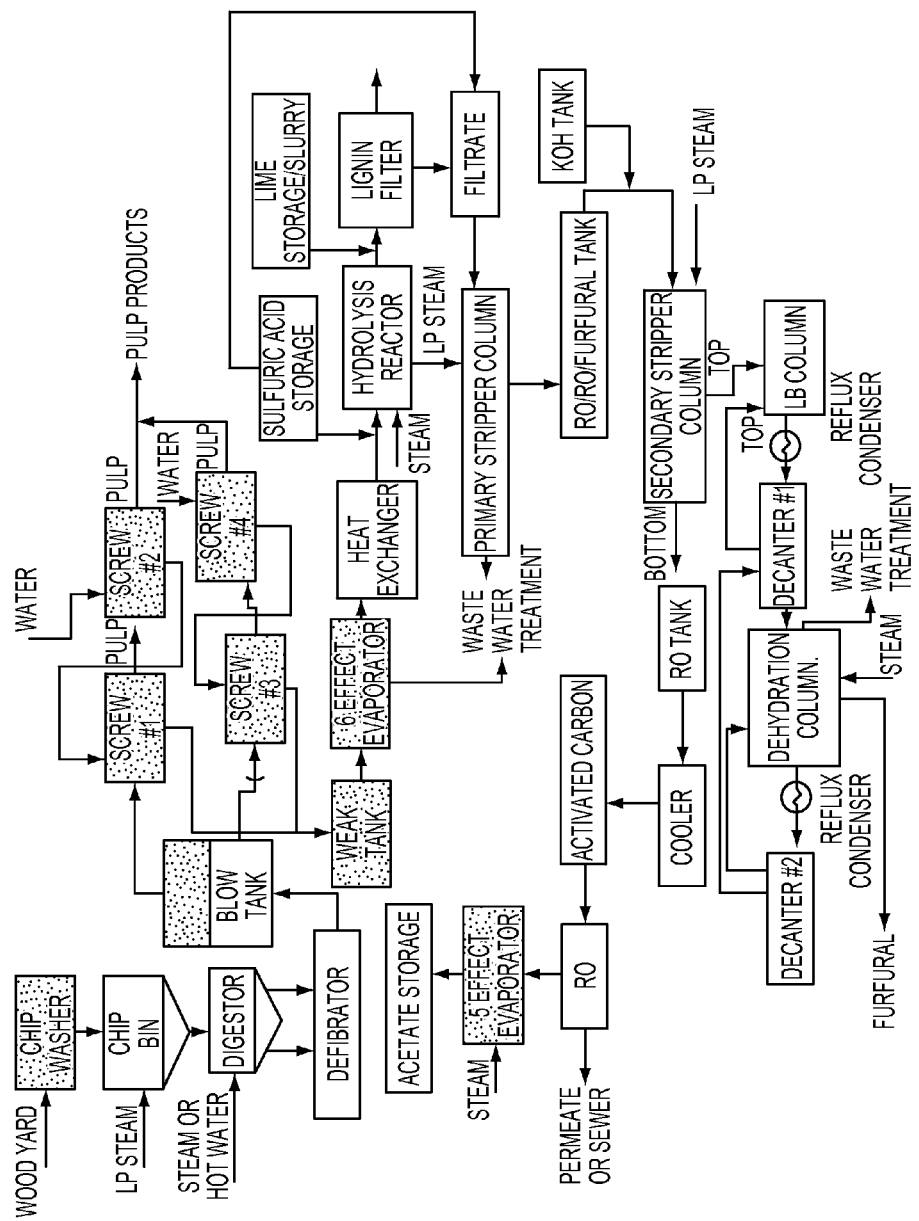
FIG. 4 is a simplified process-flow diagram for the production of pulp, acetates, and furfural, in some embodiments.

FIG. 2 is a simplified process-flow diagram for the production of pulp, hemicelluloses, and acetates, in some embodiments. FIG. 3 shows a simplified process-flow diagram for the production of pulp, sugars, and acetates, in some embodiments. FIG. 4 shows a simplified process-flow diagram for the production of pulp, acetates, and furfural, in some embodiments. These figures by no means limit the invention and are meant to be exemplary only. Additional unit operations may be included. For example, additional digestors for HWE pulping may be employed anywhere in the processes depicted.

In some embodiments, washing of HWE pulp is performed using fresh water. In some embodiments, washing of HWE pulp is performed using recycled water that does not contain significant quantities of alkali. The absence of significant quantities of alkaline components reduces or avoids caustic degradation of sugars.

HWE pulping typically will produce digested solids in liquid with a pH of about 3 to 5, such as from about 3.5 to 4.5. In some embodiments, following HWE pulping, the pH of the pulp is adjusted prior to refining of the solids. In certain embodiments, the pH is adjusted to neutral or near-neutral pH, such as pH selected from about 5 to about 9, preferably about 6.5-7.5, more preferably about 6.8-7.2. The pH adjustment may be accomplished by any known means, such as (but not limited to) treatment with sodium hydroxide or ammonia.

In some embodiments, following HWE pulping, an additional pulping step is employed, such as soda (sodium carbonate) pulping. In some embodiments, the hydrolysate (containing hemicelluloses) from HWE pulping is separated from the solids prior to introducing soda to the solids.

FIGS. 5A and 5B summarize pulp physical properties measured from laboratory-scale trials for a range of HWE pulping conditions. In these figures, LHW is "liquid hot water." Soda cooks were performed for comparison. The results in FIG. 5A were used to adjust and optimize conditions for the experiments in FIG. 5B. Note that in FIG. 5B, the refining pH is about 7 to 7.3, compared to a refining pH range of about 3.8 to 4.2 in the HWE experiments. FIG. 6 summarizes the data collected with respect to the hemicellulose stream extracted during HWE pulping.

The HWE pulp obtained may be combined with another biomass source prior to downstream processing. For example, the HWE pulp may be combined with recycled fiber (e.g., OCC or old corrugated container pulp) and then fed to a paper machine, in some embodiments. Or, the HWE pulp may be combined with a NSSC pulp, soda pulp, sulfite pulp, Kraft pulp, or another pulp for further processing.

In some embodiments, the process further comprises removing a vapor stream comprising water and vaporized acetic acid from the extract liquor in at least one evaporation stage at a pH of 4.8 or less, to produce a concentrated extract liquor comprising the fermentable hemicellulosic sugars. At least one evaporation stage is preferably operated at a pH of 3.0 or less.

The process may further comprise a step of fermenting the fermentable hemicellulosic sugars to a fermentation product. The fermentation product may be ethanol, 1-butanol, isobutanol, or any other product (fuel or chemical). Some amount of the fermentation product may be growth of a microorganism or enzymes, which may be recovered if desired.

In some embodiments, the fermentable hemicellulose sugars are recovered from solution, in purified form. In some embodiments, the fermentable hemicellulose sugars are fermented to produce biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Pentose sugars can react to produce furfural. Under conditions of heat and acid, xylose and other five-carbon sugars undergo dehydration, losing three water molecules to become furfural ($C_5H_4O_2$). Furfural is an important renewable, non-petroleum based, chemical feedstock. Hydrogenation of furfural provides furfuryl alcohol, which is a useful chemical intermediate and which may be further hydrogenated to tetrahydrofurfuryl alcohol. Furfural is used to make other furan chemicals, such as furoic acid, via oxidation, and furan via decarbonylation. Generally speaking, process conditions that may be adjusted to promote furfural include, in one or more reaction steps, temperature, pH or acid concentration, reaction time, catalysts or other additives (e.g. $FeSO_4$), reactor flow patterns, and control of engagement between liquid and vapor phases.

In some embodiments, the process further comprises recovering the lignin as a co-product, either in combination with a salt such as gypsum, or in substantially pure form.

Process integration may be carried out for any of the disclosed processes or configurations. In some embodiments, process integration includes pinch analysis and energy optimization involving one or more steps (including all steps) in the process.

For example, evaporator condensates may be recycled for use in one or more washing steps, and/or as part of the digestor cooking liquor. In some embodiments, evaporator condensates may be recycled to a reverse osmosis unit configured for recovering alkaline acetates. Process integration may also be conducted with downstream papermaking operations.

In some embodiments, process integration includes concentrating fermentable sugars, recovering a condensate stream therefrom, and introducing the condensate stream to another location with a water requirement, such as washing, filter regeneration, or fermentation. The other location may be upstream or downstream of the condensate stream, or may even be at a co-located site.

In some embodiments, process integration includes sterilizing a fermentor or fermentor feed stream with a vapor take-off from one or more evaporators used for concentrating the fermentable sugars and/or one or more evaporators used for concentrating the fermentation product. In some embodiments, process integration includes pre-cooling a fermentor feed stream with a product stream comprising the fermentation product.

In some embodiments, process integration includes concentrating the fermentation product in a non-externally-heated effect of a multiple-effect evaporation unit, such as the last effect of the multiple-effect evaporation unit. In some embodiments, process integration includes using vapor recompression and vacuum pumping to concentrate the fermentation product, to minimize cooling water requirements.

In some embodiments, process integration includes concentrating one or more organic waste streams and combusting the one or more organic waste streams with lignin or another biomass-derived material.

In some embodiments, process integration includes utilizing a rectifier reflux condensor to pre-evaporate stillage from a fermentation product distillation column. The process integration may also include preheating dimineralized water or preheating turbine condenser condensate, for example.

When lignosulfonic acid is utilized, either to assist the initial extraction or for hydrolysis of hemicellulose oligomers to monomers, the lignosulfonic acid may be provided by another biorefining process. For example, the AVAP® process employs sulfur dioxide and a solvent for lignin to fractionate biomass, which produces lignosulfonic acids during digestion.

The present invention, in various embodiments, offers several benefits including but not limited to (i) increased yield of pulp, (ii) recovery of hemicelluloses which may be converted to value-added products, (iii) removal of chemicals from the pulping process, (iv) elimination of chemical-recovery plant operations, (v) reduction in number of evaporation stages required, and (vi) reduced environmental footprint.

The present invention also provides systems configured for carrying out the disclosed processes, and compositions or products produced therefrom. Biorefineries may be configured to carry out the processes disclosed using known equipment. The biorefineries may be retrofits to existing mills, or new sites.

Any stream generated by the disclosed processes may be partially or completed recovered, purified or further treated, and/or marketed or sold.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are hereby incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent application will cover those variations as well.

What is claimed is:

1. A process for co-producing corrugated medium pulp or paper pulp as well as hemicellulosic sugars from biomass, said process comprising:
   (a) providing lignocellulosic biomass comprising cellulose, hemicellulose, and lignin;
   (b) digesting said biomass in the presence of steam and/or hot water to extract at least a portion of said hemicellulose into a liquid phase, thereby generating extracted solids, wherein step (b) does not include a chemical pulping method;
   (c) separating at least some of said liquid phase from said extracted solids;
   (d) washing said extracted solids with water at a washing pH of about 7 or less, thereby generating a liquid wash filtrate and washed solids;
   (e) separating at least some of said liquid wash filtrate from said washed solids;
   (f) refining said washed solids at a refining pH of 4 to 6.5, thereby generating corrugated medium pulp or paper pulp; and
   (g) hydrolyzing said hemicellulose contained in said liquid phase and/or in said liquid wash filtrate, in the presence of a hydrolysis catalyst, to generate hemicellulosic sugars,
   wherein step (c) is performed prior to step (d), wherein said liquid phase separated in step (c) and said liquid wash filtrate are separately processed and not later combined.

2. The process of claim 1, wherein step (b) is conducted at a digestor temperature selected from about 140° C. to about 220° C.

3. The process of claim 1, wherein step (b) is conducted at a digestor residence time selected from about 1 minute to about 60 minutes.

4. The process of claim 1, wherein step (b) is conducted at a digestor pH from about 2 to about 6.

5. The process of claim 1, wherein said corrugated medium pulp or paper pulp yield on biomass is from about 75% to about 95% by weight.

6. The process of claim 1, wherein said washing in step (d) utilizes fresh water.

7. The process of claim 1, wherein said washing in step (d) utilizes alkali-free recycled water.

8. The process of claim 1, wherein steps (b) and (d) are carried out in a single unit.

9. The process of claim 1, wherein said refining pH is selected from 4 to 6.

10. The process of claim 1, wherein said refining pH is selected from 6 to 6.5.

11. The process of claim 1, wherein said hydrolysis catalyst comprises one or more compounds selected from the group consisting of sulfur dioxide, sulfurous acid, sulfuric acid, lignosulfonic acid, and combinations or derivatives thereof.

12. The process of claim 1, wherein said hydrolysis catalyst comprises hemicellulase enzymes.

13. The process of claim 1, wherein said corrugated medium pulp or paper pulp is characterized by a concora of about 25 lbf or higher.

14. The process of claim 1, wherein said corrugated medium pulp or paper pulp is characterized by a ring crush strength of about 25 (lbf/6 in) or higher.

15. The process of claim 1, wherein said corrugated medium pulp or paper pulp is characterized by a breaking length of about 2.0 km or higher.

16. The process of claim 1, wherein at least a portion of said corrugated medium pulp or paper pulp is hydrolyzed to generate glucose.

17. The process of claim 1, said process further comprising recovering an acetic acid or acetate co-product.

18. The process of claim 1, wherein at least a portion of said corrugated medium pulp or paper pulp is converted to corrugated medium or paper.

* * * * *